(12) United States Patent
Hazama (10) Patent No.: US 10,869,675 B2
(45) Date of Patent: Dec. 22, 2020

(54) HEMOSTATIC DEVICE

(71) Applicant: TERUMO KABUSHIKI KAISHA, Tokyo (JP)

(72) Inventor: Kenichi Hazama, Bear, DE (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 375 days.

(21) Appl. No.: 15/642,811

(22) Filed: Jul. 6, 2017

(65) Prior Publication Data

US 2018/0008281 A1    Jan. 11, 2018

(30) Foreign Application Priority Data

Jul. 6, 2016 (JP) ................. 2016-134599

(51) Int. Cl.
*A61B 17/135* (2006.01)
*A61B 17/132* (2006.01)
*A61B 17/00* (2006.01)

(52) U.S. Cl.
CPC ........ *A61B 17/135* (2013.01); *A61B 17/1325* (2013.01); *A61B 2017/00526* (2013.01); *A61B 2017/00831* (2013.01); *A61B 2017/00907* (2013.01)

(58) Field of Classification Search
CPC .............. A61B 17/132; A61B 17/1322; A61B 17/1325; A61B 17/135; A61B 17/1355; A61B 2017/12004; A61B 17/1327; A61B 5/022; A61B 5/02233; A61B 5/02241; A61H 9/0078; A61H 9/0085; A61H 9/0092

USPC .................................................. 606/201–204
See application file for complete search history.

(56) References Cited

U.S. PATENT DOCUMENTS

| 7,498,477 | B2* | 3/2009 | Wada ................. A61B 17/1325 602/53 |
| 8,481,803 | B2 | 7/2013 | Wada et al. |
| 8,524,974 | B2 | 9/2013 | Wada et al. |
| 8,759,603 | B2 | 6/2014 | Wada et al. |
| 9,332,994 | B2* | 5/2016 | Pancholy ........... A61B 17/1325 |
| 9,427,239 | B2* | 8/2016 | Benz .................... A61B 17/135 |
| 2004/0098035 | A1 | 5/2004 | Wada et al. |
| 2015/0217100 | A1* | 8/2015 | Karino ................... A61B 1/307 604/22 |
| 2016/0338709 | A1 | 11/2016 | Wada et al. |

FOREIGN PATENT DOCUMENTS

JP          2004-201829 A      7/2004

* cited by examiner

*Primary Examiner* — Martin T Ton
(74) *Attorney, Agent, or Firm* — Buchanan Ingersoll & Rooney PC (57) ABSTRACT

A hemostatic device has a band for being wrapped around a puncture site of a wrist, securing means for securing the band in a state where the band is wrapped around the wrist, and an inflation portion that interlocks with the band, and that is inflated by injecting gas. The inflation portion includes a first region which stretches when the gas is injected into the inflation portion, and a second region which is less likely to stretch compared to the first region and which is formed of a rigid material. The second region has a micropore which discharges the gas contained in the inflation portion with the lapse of time, in a state where the inflation portion is inflated.

17 Claims, 7 Drawing Sheets

HEMOSTATIC DEVICE

CROSS-REFERENCE TO RELATED APPLICATIONS

This application claims priority to Japanese Application Number 2016-134599 filed on Jul. 6, 2016, the entire content of which is incorporated herein by reference.

TECHNICAL FIELD

The disclosure herein relates to a hemostatic device used for performing hemostasis by compressing a punctured site.

BACKGROUND DISCUSSION

In recent years, percutaneous treatment and examination have been performed in which a blood vessel in the arms or legs is punctured and an introducer sheath is introduced into a puncture site so as to deliver a medical device such as a catheter to a lesion area via a lumen of the introducer sheath. In a case where these treatments and examinations are performed, an operator needs to perform hemostasis at the puncture site after the introducer sheath is removed therefrom. In order to perform hemostasis, a known hemostatic device is used, which includes band for being wrapped around a limb such as the arms and legs, securing means for securing the band in a state where the band is rapped around the limb, and an inflation portion that interlocks with the band, and that is inflated by injecting a fluid so as to compress the puncture site.

According to such a hemostatic device, if the inflated inflation portion continues to strongly compress the puncture site and a blood vessel or a nerve around the puncture site for a long time, there is a possibility that numbness or pain may be caused or the blood vessel may be occluded. In order to prevent the vascular occlusion, a physician or a nurse generally inflates the inflation portion, Thereafter, he or she periodically connects a dedicated instrument such as a syringe to the hemostatic device, discharges a fluid contained inside the inflation portion, and performs a decompressing operation for reducing internal pressure of the inflation portion, thereby reducing the compressing force acting on the puncture site with the lapse of time.

In contrast, according to the hemostatic device disclosed in JP-A-2004-201829 the inflation portion is configured to include a material which stretches with the lapse of time. Therefore, after the inflation portion is inflated by injecting the fluid into the inflation portion, the inflation portion is gradually inflated and deformed by pressure applied from the fluid inside the inflation portion. Whereas the amount of the fluid inside the inflation portion does not substantially decrease, the volume of an internal space of the inflation portion gradually increases. Accordingly, the internal portion pressure of the inflation portion can be reduced with the lapse of time. In this manner, the compressing force acting on the puncture site can be reduced with the lapse of time.

According to the hemostatic device disclosed in JP-A-2004-201829, the physician or the nurse can save time and effort when performing the decompressing operation. However, if the inflation portion is configured to include the material which stretches with the lapse of time, the inflation portion is progressively inflated and deformed with the lapse of time. As a result, a thickness of the inflation portion becomes thinner. From a viewpoint of satisfactorily maintaining strength of the inflation portion, it is conceivable that the thickness of the inflation portion is preferably maintained to some extent.

For example, as an alternative method of the above-described decompressing method utilizing a property of the configuration material of the inflation portion, a method is conceivable in which a hole is formed in the inflation portion itself so as to discharge gas via the hole. However, if the hole is formed in the inflation portion itself, an inner diameter of the hole or a channel length (length in a thickness direction of the inflation portion) is changed before and after the inflation portion is inflated, consequently, it becomes difficult to adjust a discharge rate (discharge amount) of the gas. Therefore, the hemostatic device is less likely to realize a desired decompressing protocol for reducing the compressing force with the lapse of time in accordance with hemostatic progress while preventing the vascular occlusion.

SUMMARY

The disclosure herein is directed to a hemostatic device which can satisfactorily maintain strength of an inflation portion and can easily adjust a gas discharge rate.

In order to achieve the same, the disclosure provides a hemostatic device having a band for being wrapped around a hemostasis-requiring site of a limb, securing means for securing the band in a stag where the band is wrapped around the limb and an inflation portion that interlocks with the band, and that is inflated by injecting gas. The inflation portion includes a first region which stretches when the gas is injected into the inflation portion, and a second region which is less likely to stretch compared to the first region and which is formed of a rigid material. The second region has a micropore which discharges the gas contained in the inflation portion with the lapse of time, in state where the inflation portion is inflated.

As described above, the micropore of the inflation portion is disposed in the second region which is more rigid than the first region. In this manner, in the micropore before and after the inflation portion is inflated, an inner diameter and a channel length (length in a thickness direction of the inflation portion) of the micropore are less likely to be changed. Therefore, in view of a viscosity of the gas used for dilating the inflation portion, the inner diameter of the micropore is formed to have a predetermined size. In this manner, it is possible to easily adjust a gas discharge rate of the inflation portion. Furthermore, the gas is discharged from the second region via the micropore. Accordingly, it is not necessary to manufacture the inflation portion so that the thickness of the inflation portion becomes thinner with the lapse of time. Therefore, the hemostatic device according to the present invention can satisfactorily maintain strength of the inflation portion, and easily perform decompressing adjustment for reducing a compressing force with the lapse of time in accordance with hemostatic progress while preventing vascular occlusion.

BRIEF DESCRIPTION OF THE DRAWINGS

FIGS. 3(A)-3(C) are plan views for describing a configuration of an inflation portion of the hemostatic device according to the exemplary embodiment

DETAILED DESCRIPTION

Hereinafter, an exemplary embodiment of the disclosure and modified examples thereof will be described with reference to the accompanying drawings. Note that, the following description does not limit the technical scope or the meaning of terms described in the appended claims. In addition, dimensional proportions in the drawings are exaggerated and may be different from actual proportions for convenience of description, in some cases.

Figure 4:
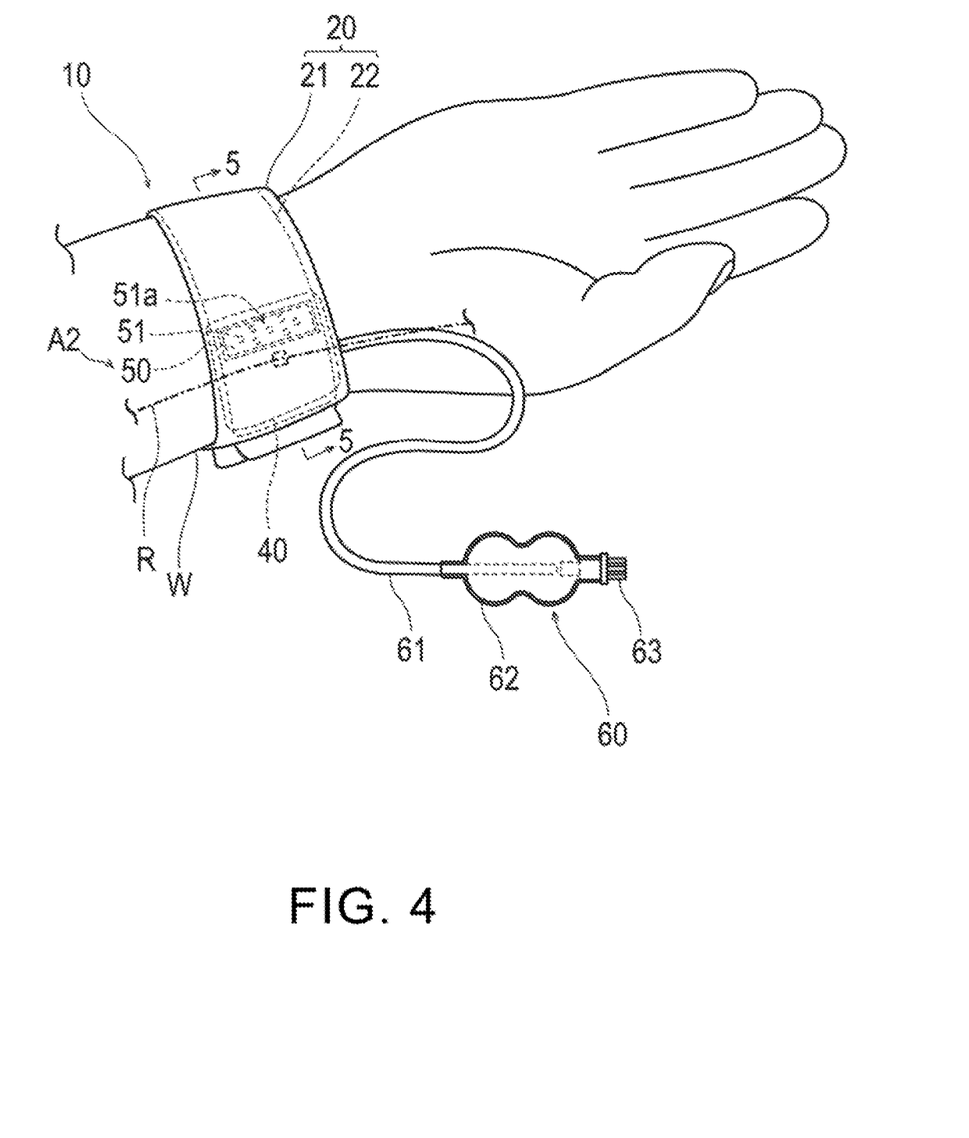
FIG. 4 is a perspective view illustrating a state where the hemostatic device according to the exemplary embodiment is worn on a wrist.
Figure 5:
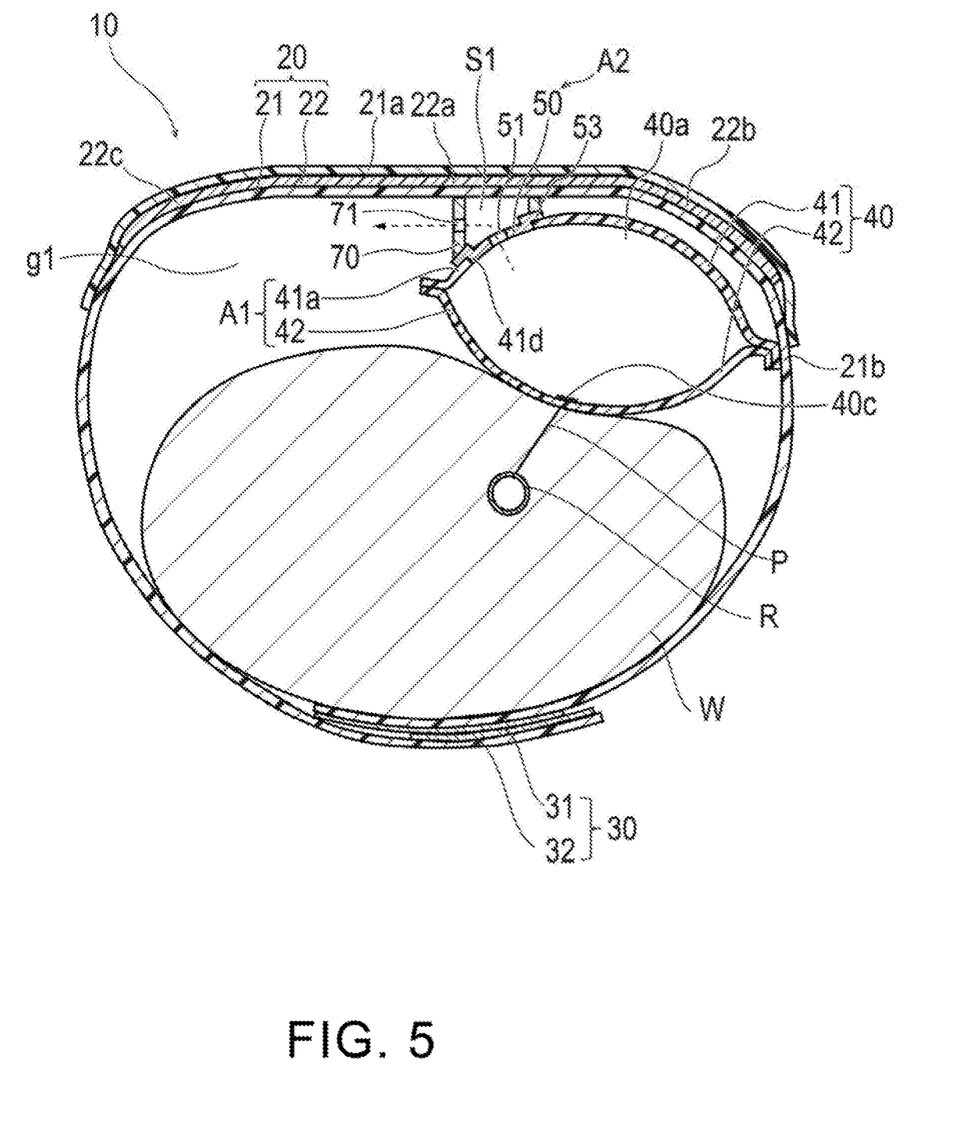
FIG. 5 is a sectional view taken along line 5-5 in FIG. 4.

As illustrated in FIGS. 4 and 5, a hemostatic device 10 according to the exemplary embodiment of the disclosure herein is used for performing hemostasis on a puncture site P (corresponding to a "hemostasis-requiring site") formed in a radial artery R of a wrist W (corresponding to a "limb") in order to insert a catheter for performing treatment and examination into a blood vessel, after an introducer sheath indwelling the puncture site P is removed.

Figure 1:
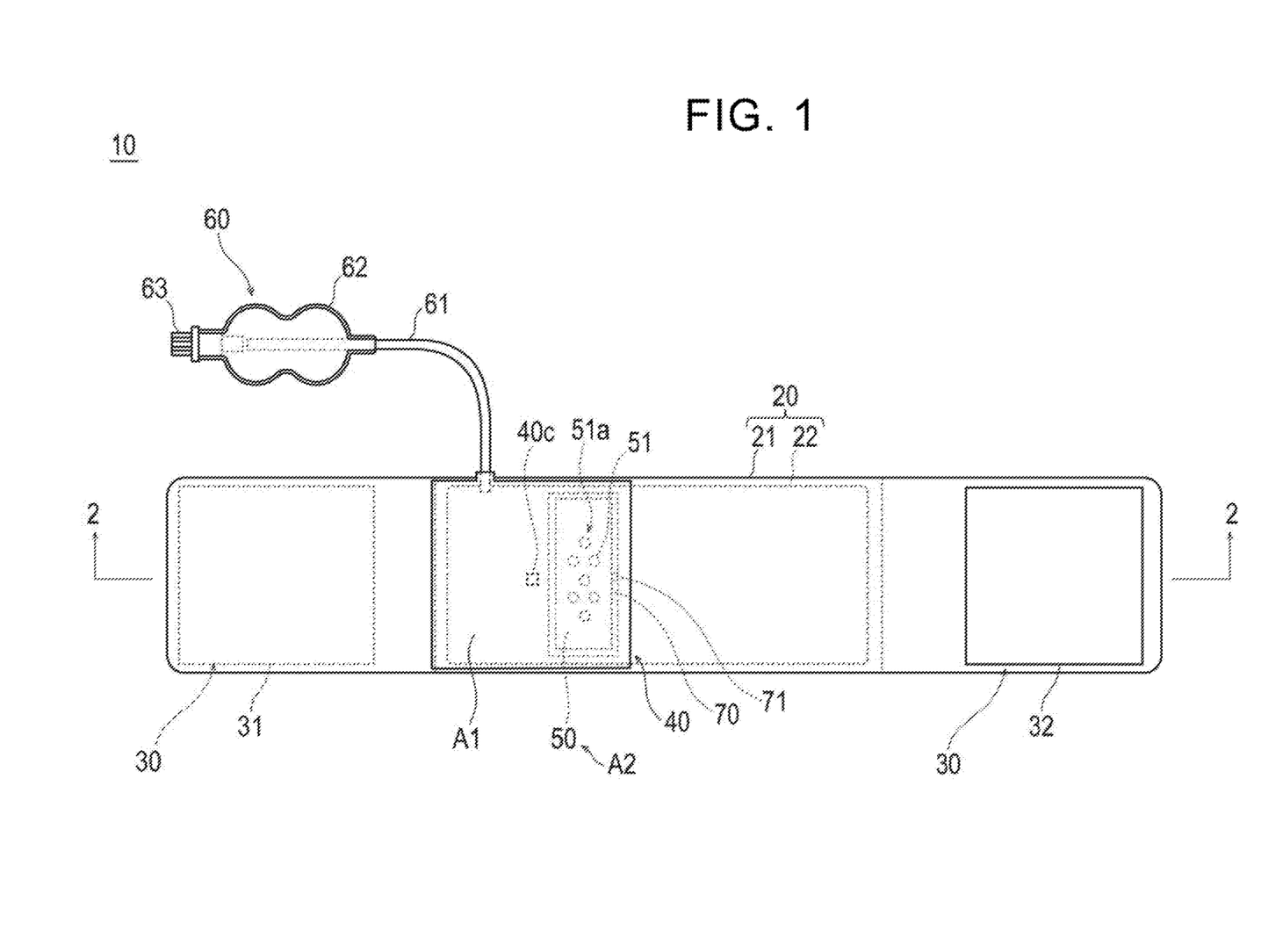
FIG. 1 is a plan view when a hemostatic device according n exemplary embodiment of the disclosure is viewed from an inner surface side.
Figure 2:
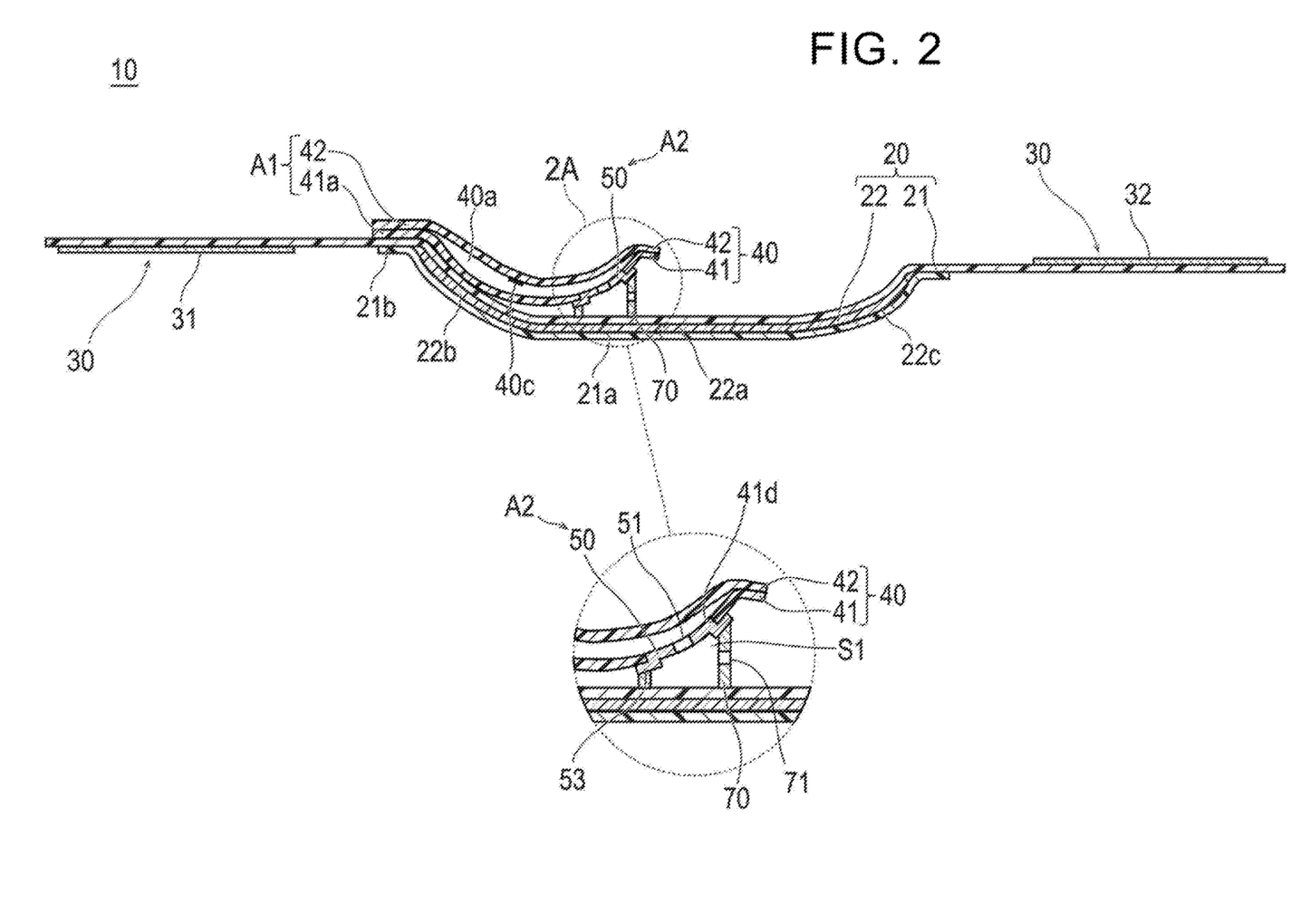
FIG. 2 is a sectional view taken along line 2-2 in FIG. 1.

As illustrated in FIGS. 1 and 2, the hemostatic device 10 has a band 20 for being wrapped around the wrist W, a surface fastener 30 (corresponding to "securing means") for securing the band 20 in a state where the band 20 is wrapped around the wrist W, an inflation portion 40 that is inflated by injecting gas so as to compress the puncture site P, a marker 40c for aligning the inflation portion 40 with the puncture site P, and an injection portion 60 that can inject gas into the inflation portion 40.

Note that FIG. 2 illustrates a sectional view taken along arrow line 2-2 illustrated in FIG. 1, and illustrates an enlarged view of a portion surrounded by broken line portion 2A in FIG. 2.

In the description herein, when the band 20 is in a state of being wrapped around the wrist W, a side (wearing surface side) facing a body surface of the wrist W in the band 20 is referred to as an "inner surface side", and a side opposite thereto is referred to as an "outer surface side".

The band 20 includes a belt 21 configured to include a flexible belt-like member, and a support plate 22 which is more rigid than the belt 21.

As illustrated in FIGS. 4 and 5, the belt 21 is wrapped substantially one time around an outer periphery of the wrist W. As illustrated in FIG. 2, a support plate holder 21a for holding the support plate 22 is formed in a central portion of the belt 21. The support plate holder 21a is adapted to have a double layer construction n such a way that a separate belt-like member is joined to the outer surface side (or the inner surface side) by means of fusion bonding (heat-welding, high frequency fusion, or ultrasound fusion) or adhesion (adhesion using an adhesive or a solvent), thereby holding the support plate 22 inserted into a gap or pocket formed between the double layer structure.

A male side (or a female side) 31 of a surface fastener 30 such as, a hook and loop fastener (e.g., a product commonly known as VELCRO® or Magic Tape in Japan, is disposed on the outer surface side of a portion in the vicinity of the left end in FIG. 1 of the belt 21 and a female side (or a male side) 32 of the surface fastener 30 is disposed on the inner surface side of a portion in the vicinity of the right end in FIG. 1 of the belt 21. As illustrated in FIG. 4, the belt 21 is wrapped around the wrist W, and the male side 31 and the female side 32 are joined to each other. In this manner, the band 20 is worn on the wrist W. Note that, without being limited to the surface fastener 30, means for securing the band 20 in a state where the band 20 is wrapped around the wrist W may be a snap, a button, a clip, or a frame member passing through the end portion of the belt 21, for example.

It is preferable that the belt 21 is configured to include a resin material which can interlock with, the first region A1 of the inflation portion 40 (to be described later) by means of fusion bonding. Note that, the belt 21 may adopt any configuration as long as an interlock region 21b (in the exemplary embodiment, as illustrated in FIG. 2, a region between a region where a first curved portion 22b of the support plate 22 (to be described later) is disposed and a region to which the male side 31 of the surface fastener 30 is attached) with which at least the inflation portion 40 interlocks configured to include a resin material which can be fused to the inflation portion 40. A portion other than the interlock region 21b may be formed of a material other than the resin material which can be fused to the inflation portion 40.

In addition, for example, as a material of the belt 21, it is possible to use a thermoplastic material formed of a thermoplastic resin such as polyvinyl chloride, polyethylene, polypropylene, and polyvinylidene chloride, or various thermoplastic elastomers such as olefinic thermoplastic elastomer and styrene thermoplastic elastomer. Since the belt 21 is formed of this material, the belt 21 is relatively less likely to stretch. Without being affected by a wearer's size of the wrist W, it is possible to suitably maintain a state where the inflation portion 40 is wrapped around the wrist W. In addition, in a case where the first region A1 of the inflation portion 40 (to be described later) is formed of the thermoplastic material, the first region A1 can be interlocked with the inflation portion 40 by means of fusion bonding.

It is preferable that a portion overlapping at least the inflation portion 40 in the belt 21 is substantially transparent. However, without being limited to transparency, the portion may be translucent or colored transparent. In this manner, the puncture site P is visible from the outer surface side, thereby enabling the marker 40c (to be described later) to easily align with the puncture site P.

As illustrated in FIG. 2, the support plate 22 is inserted between the support plate holder 21a formed to have the double layer structure in the belt 21. In this manner, the support plate 22 is held by the belt 21. The support plate 22 has a plate shape in which at least a portion thereof is curved toward the inner surface side (wearing surface side). The support plate 22 is configured to include a material which is more rigid than that of the belt 21 and, is adapted to maintain a substantially constant shape. The method of providing the support plate 22 on the belt 21 is not ted to the illustrated arrangement, however, and may involve joining the support plate 22 to the inner surface side or the outer surface side of the band 20 by a suitable method such as welding or adhesion. Also, another acceptable arrangement is one in which the belt 21 is connected to both ends of the support plate 22. It is thus not essential for a portion of the belt 21 to overlap with the support plate 22.

The support plate 22 has a long shape in the longitudinal direction of the belt 21. A central portion 22a in the longitudinal direction of the support plate 22 is hardly curved, and has a flat plate or generally planar shape. Both sides of the central portion 22a respectively have a first curved portion 22b (left side in FIG. 2) and a second curved portion 22c (right side in FIG. 2) which ere curved toward the inner surface side and along the longitudinal direction (circumferential direction of the wrist W) of the belt 21.

By way of example, configuration materials of the support plate 22 include acrylic resin, polyvinyl chloride (particularly, rigid polyvinyl chloride), polyethylene, polypropylene, polyolefin such as polybutadiene, polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, polyethylene terephthalate (PET), polyester such as polybutylene terephthalate (PBT), butadiene-styrene copolymer, aromatic or aliphatic polyimide, and fluorine-based resin such as polytetrafluoroethylene.

Similar to the belt 21, in the support plate 22 it is preferable that a portion overlapping the inflation portion 40 is substantially transparent. However, without being limited to transparency, the portion may be translucent or colored transparent. In this manner, the puncture site P is reliably visible from the outer surface side, thereby enabling the marker 40c (to be described later) to easily align with the puncture site P. Note that, the support plate 22 may not have a flat plate portion like the central portion 22a, and may be curved over the entire length.

The inflation portion 40 is provided with a function to apply a compressing force to the puncture site P after being inflated by injecting gas, and a function to reduce the compressing force acting on the puncture site P with the lapse of time by discharging the injected gas outward with the lapse of time. Note that, as long as the inflation portion 40 can be inflated, the gas injected into the inflation portion 40 is not particularly limited. For example, air can be used.

As illustrated in FIG. 2, the inflation portion 40 has the first region A1 which stretches when the gas is injected into the inflation portion 40, and the second region A2 which is much less likely to stretch than the first region A1 and which is formed of a rigid material. According to the exemplary embodiment, the first region A1 is formed of a resin material, and the second region A2 is formed of a metal material. In the description herein, the description of "the second region A2 which is much less likely to stretch than the first region A1" means that a material of the second region A2 has the smaller Young's modulus (tensile elastic modulus) than the first region A1.

As illustrated in FIG. 2, the inflation portion 40 is formed in a bag shape in which a first sheet 41 and a second sheet 42 overlap each other. As illustrated in FIG. 5, an inflation space 40a into which the gas can be injected is formed inside the inflation portion 40.

Figure 3A:
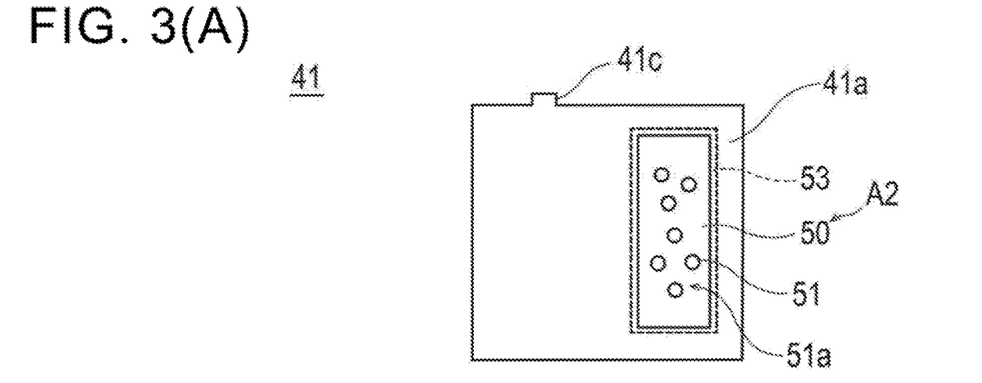
FIG. 3(A) is a view illustrating a first sheet configuring the inflation portion.
Figure 3B:
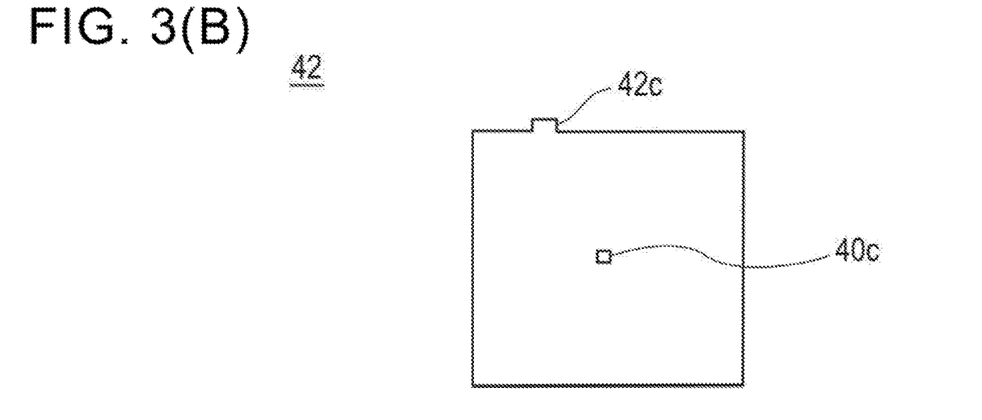
FIG. 3(B) is a view illustrating a second sheet configuring the inflation portion.
Figure 3C:
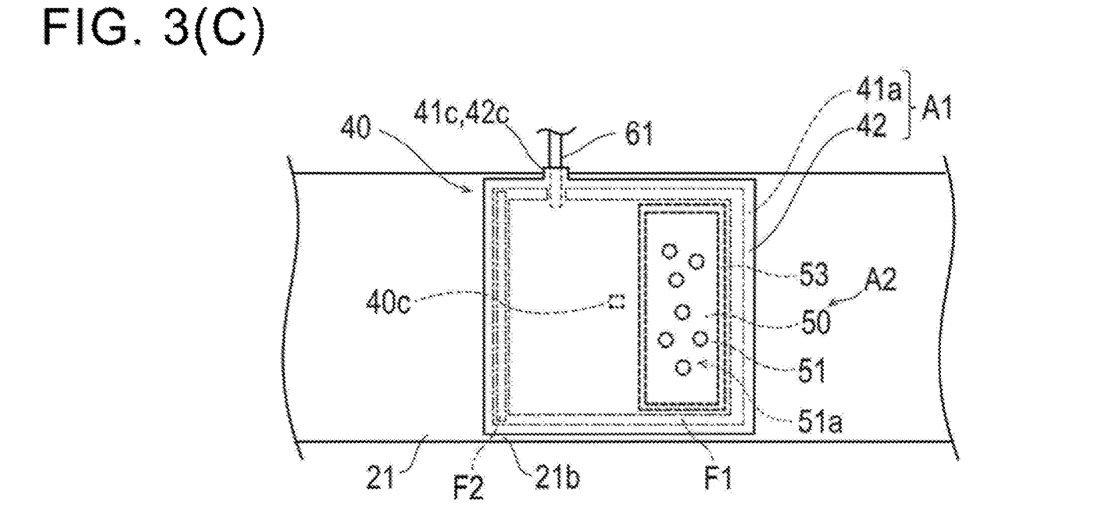
FIG. 3(C) is a plan view illustrating an interlock position of a band interlocking with the inflation portion.

FIG. 3(A) illustrates the first sheet 41 in a state before the inflation portion 40 is formed. FIG. 3(B) illustrates the second sheet 42 in a state before the inflation portion 40 is formed. FIG. 3(C) illustrates a state where the inflation portion 40 configured to include the respective sheets 41 and 42 interlocks the belt 21 of the band 20.

Note that, an interlock form between the band 20 and the inflation port on 40 is not particularly limited. For example, the form of the interlock may include that the band 20 and the inflation portion 40 are directly secured to (interlock with) each other, and that the inflation portion 40 interlocks with the band 20 via a tube 61 of the injection portion 60 secured to the band 20.

In a plan view as illustrated in FIG. 3(A), the first sheet 41 includes a substantially rectangular outer shape. The first sheet 41 has a protruding portion 41c protruding outward from a rectangular portion.

In a plan view as illustrated in FIG. 3(B), the second sheet 42 includes a substantially rectangular outer shape. The second sheet 42 has a protruding portion 42c protruding outward from the rectangular portion. In addition, a substantially central portion of the second sheet 42 in a plan view has the marker 40c.

As illustrated in FIG. 3(C), the tube 61 of the injection portion 60 (to be described later) is disposed between the protruding portion 41c of the first sheet 41 and the protruding portion 42c of the second sheet 42. Then the respective protruding portions 41c and 42c adhere to the tube 61 by using an adhesive. In this manner, the tube 61 is held in the inflation portion 40. Note that, each outer shape of the first sheet 41 and the second sheet 42 is not particularly limited to the above-described rectangular shape. For example, circular, elliptical, and polygonal shapes may be employed. In addition, the protruding portions 41c and 42c may not be disposed therein.

As illustrated in FIG. 3(A) the first sheet 41 has a flexible portion 41a formed of a resin material, and a rigid portion 50 joined to the flexible portion 41a. On the other hand, as illustrated in FIG. 3(B), the second sheet 42 is configured to, include a sheet-like member whose entire body is formed of a resin material such that the second sheet 42 is flexible.

As illustrated in FIG. 3(C), a peripheral edge portion (flexible portion 41a) of the first sheet 41 and a peripheral edge portion of the second sheet 42 are joined to each other by a first joint portion F1 in a state where the first sheet 41 and the second sheet 42 overlap each other. For example, joining can be performed using an adhering method using fusion bonding or an adhesive.

The first region A1 of the inflation portion 40 is configured to include a region formed of a resin material of the inflation portion 40. That is, in the inflation portion 40, a region in which the flexible portion 41a of the first sheet 41 and the second sheet 42 are disposed services as the first region A1.

As illustrated in FIG. 3(C), at least a portion of the first region A1 and the interlock region 21b of the belt 21 are joined to each other by a second joint portion F2. As illustrated in FIG. 2, the inflation portion 40 is disposed in a state where the first sheet 41 faces the inner surface side of the band 20. Accordingly, one side in the peripheral edge portion of the first sheet 41 and the inner surface side of the interlock region 21b of the band 20 are joined to each other.

For example, as a resin material for forming the first region A1, it is possible to use a thermoplastic resin such as polyvinyl chloride, polyethylene, polypropylene, polyvinylidene chloride, or various thermoplastic elastomers such as olefinic thermoplastic elastomer and styrene thermoplastic elastomer.

Note that, the resin material used for the flexible portion 41a of the first sheet 41 and the resin material used for the interlock region 21b of the band 20 employ the same thermoplastic material, and both the resin materials are fused to each other in the second joint portion F2. In this manner, a binding force between the first sheet 41 and the band 20 can be strengthened. However, the resin material used for the flexible portion 41a of the first sheet 41 and the resin material used for the interlock region 21b of the band 20 may be different from each other. In addition, the resin material used for the flexible portion 41a of the first sheet 41 and the resin material used for the second sheet 42 employ the same thermoplastic material. In this manner, the binding force between the first sheet 41 and the second sheet 42 in first joint portion F1 can be strengthened. However, the resin material used for the flexible portion 41a of the first sheet 41 and the resin material used for the second sheet 42 may be different from each other.

In a case where the first region A1 is configured to include the resin material, it is preferable that the first region A1 is configured to include the resin material other than a thermosetting elastomer. In general, the thermosetting elastomer has more gas permeation amount based on gas dissolution and diffusion phenomenon than the thermoplastic material. Accordingly, if the first region A1 is configured to include the thermosetting elastomer, a gas discharge amount discharged from the first region A1 increases. For this reason, a micropore 51 (to be described later) becomes less likely to adjust the gas discharge amount. Therefore, in a case where the first region A1 is configured to include the resin material, it is preferable that the first region A1 is formed of the resin material other than the thermosetting elastomer.

For example, as the metal material for forming the second region A2, it is possible to use known metal materials such as aluminum, copper, stainless steel, iron, an alloy obtained by mixing two or more predetermined types of metal. However, any material may be used as long as the material for forming the second region A2 is more rigid than the material for forming at least the first region A1. Therefore, the material for forming the second region A2 can be appropriately changed in view of a relationship with the material for forming the first region A1. For example, as a material other than the metal material, it is possible to use alumina, ceramic such as silica, a resin material such as thermosetting elastomer, or glass.

As illustrated in the enlarged view in FIG. 2, the first sheet 41 has a through-hole 41d penetrating a thickness direction of the first sheet 41. The rigid portion 50 of the first sheet 41 is disposed so as to cover the through-hole 41d, and a peripheral edge portion 53 thereof is joined to the first sheet 41.

The second region A2 of the inflation portion 40 is configured to include a region where the rigid portion 50 is disposed in the first sheet 41.

The second region A2 has the micropore 51 which discharges the gas contained in the inflation portion 40 with the lapse of time in a state where the inflation portion 40 is inflated. The micropore 51 communicates with the inflation space 40a of the inflation portion 40. A broken line arrow in FIG. 5 illustrates a state where air is discharged from the micropore 51.

The second region A2 has a plurality of micropores 51. The reference numeral 51a illustrated in each drawing represents a single group of micropores 51, that is, the plurality of micropores (refer to FIG. 1). In the exemplary embodiment, the respective micropores 51 have the same structure. Accordingly, one micropore will be described, and description of other micropores will be omitted.

It is preferable that the micropore 51 (the plurality of micropores 51a) belonging to the second region A2 is formed so as to be capable of realizing a decompressing protocol satisfying Conditions 1 and 2 below.

(Condition 1) In a state where the band 20 is wrapped around the wrist W, the gas has to be discharged outward from the inflation portion 40 via the second region A2 over 4 hours after the inflation portion 40 is inflated. After every one hour elapses internal pressure of the inflation portion 40 reaches 70% to 97% (preferably, 75% to 94%) of the internal pressure of the inflation portion 40 one hour ago; (Condition 2) In a state where the band 20 is wrapped around the wrist W the internal pressure inside the inflation portion 40 after 4 hours elapses from the inflation reaches 30% to 80% (preferably, 40% to 71%) of the initial internal pressure.

An inner diameter of the micropore 51 can be formed so as to be capable of realizing the decompressing protocol described as an example, in accordance with the number of micropores 51 disposed in the second region A2 the thickness of the second region A2, material quality for forming the second region A2, and a use condition (pressure difference between the inside and the outside of the inflation portion 40 during hemostasis) when the hemostatic device 10 is used. Note that, in a case where the second region A2 has the plurality of micropores 51a as in the exemplary embodiment, the inner diameters may be different for each micropore 51. In this manner, the gas discharge amount of the second region A2 can be adjusted. Alternatively, the gas discharge amount of the second region A2 can be adjusted by adjusting the arrangement (distribution) of the micropores 51.

As described above, as long as the inner diameter of the micropore 51 can realize a desired decompressing protocol, the inner diameter is not particularly limited. However, for the following reason, it is preferable that the diameter is formed to be 1 nm to 10 μm, for example.

In a case where the second region A2 is configured to include the resin material, due to characteristics of the resin material, not only the gas is discharged from the micropore 51, but also gas permeation occurs based on dissolution and diffusion phenomenon of the gas passing through the second region A2. As a leading method of discharging the gas by using the micropore 51, in order to facilitate the adjustment of the gas discharge amount, it is preferable to set the inner diameter of the micropore 51 so as to discharge the gas so that the discharge amount is equal to or more than the gas permeation based on the dissolution and diffusion phenomenon. In addition, in view of processing precision when the micropore 51 is formed in the second region A2, it is preferable that the inner diameter of the micropore 51 is 1 nm or larger. On the other hand, if the inner diameter of the micropore 51 excessively increases, durability of the second region A2 becomes poor, and the desired decompressing protocol is less likely to be realized. Accordingly, it is preferable that the inner diameter of the micropore 51 is 10 μm or smaller.

Note that, for example, in a case where the second region A2 is formed of ceramics or glass instead of the metal material of the exemplary embodiment discussed above, the gas permeation hardly occurs in the thickness direction in the second region A2 Accordingly, it is possible to form the inner diameter of the micropore 51 to be smaller than 1 nm. However, even in this case, from a viewpoint of ensuring the processing precision of the micropore 51 it is preferable to form the inner diameter of the micropore 51 so as to be equal to or larger than 1 nm.

A method of forming the micropore 51 in the second region A2 can be appropriately selected depending on a material for forming the second region A2. For example, press processing, laser processing, or ion beam processing can be used. For example, in a case where the second region A2 is formed of a metal material, ceramics, or glass, the micropore 51 can be formed using laser irradiation. In a case where the micropore 51 is formed using the laser irradiation, the inner diameter of the micropore 51 can be easily and accurately adjusted, thereby facilitating manufacturing work. In addition, for example, in a case where the second region A2 is formed of the resin materials a through-hole penetrating the second region A2 in the thickness direction is formed using a puncture tool provided with a small diameter needle portion. In this manner, the micropore 51 can be formed.

As illustrated in FIG. 2, the inflation portion 40 has, a projection portion 70 disposed so as to surround the micropore 51. In a plan view illustrated in FIG. 1, the projection portion 70 is disposed so as to surround the entire periphery of the second region A.

Note that, for example, the projection portion 70 may not be secured to the band 20, or a gas discharge path 71 may net always be formed. In a case where the projection portion 70 is configured in this way, the projection portion 70 can have a slit which forms the gas discharge path 71 by being pressed against the inner surface of the band 20 when the inflation portion 40 is inflated.

As illustrated in FIG. 2 the projection portion 70 forms a space S1 surrounded by the projection portion 70 and the belt 21 of the band 20, around the plurality of micropores 51a of the second region A2.

As illustrated in FIG. 2, the projection portion 70 includes the gas discharge path 71. The gas discharge path 71 causes the gas discharged from the inflation portion 40 through the micropore 51 to be discharged from the space S1. The gas discharge path 71 is formed by a through-hole penetrating the projection portion 70 in a direction intersecting an extending direction (protruding direction) of the projection portion 70. However, as long as the gas can be discharged from the space S1, a structure of the gas discharge path 71 is not particularly limited. For example, the gas discharge path 71 may be a concave-shaped groove forming a gap through which the gas can be distributed between the projection portion 70 and the second region A2, or between the projection portion 70 and the belt 21.

In addition, the projection portion 70 may be disposed so as to surround the entire periphery in the circumferential direction of the micropore 51 (the plurality of micropores 51a) formed in the second region A2. Alternatively, the projection portion 70 may be disposed so as to surround a partial range in the circumferential direction of the micropore 51. In a case where the projection portion 70 is disposed in this way, the gas discharge path 71 can be formed by a portion (notched portion) which does not surround the micropore 51 of the projection portion 70.

As illustrated in FIG. 5, the gas discharge path 71 is formed so as to be open while facing the central portion 22a side of the support plate 22 from the space S1. Therefore, the air discharged from the gas discharge path 71 is discharged toward a gap g1 side formed between the belt 21 and the outer surface of the wrist W when a wearer wears the hemostatic device 10. In this manner, the air discharged from the inflation portion 40 can be prevented from entering between the inflation portion 40 and the belt 21.

Note that, a position for forming the gas discharge path 71 in the projection portion 70, the number of the gas discharge paths 71 formed in the projection portion 70, and the inner diameter of the gas discharge path 71 are not particularly limited as long as the gas can be discharged from the inflation portion 40.

As illustrated in FIG. 5, the projection portion 70 matches the inflated outer shape of the inflation portion 40. The height (thickness) dimension of an end portion of the projection portion on a side (left side in FIG. 5) spaced from the central portion of the cross section of the inflation portion 40 illustrated in FIG. 5 is formed to be higher than the height dimension of an end portion of the projection portion on a side (right side in FIG. 5) closer to the central portion of the cross section of the inflation portion 40. When the inflation portion 40 is inflated and deformed, the inflation portion 40 has a sectional shape whose thickness dimension decreases from the central portion to both right and left sides in the drawing. Therefore, the distance between the inflation portion 40 and the belt 21 can be maintained to be a proper size by increasing the height dimension on the side spaced from the central portion of the inflation portion 40 of the projection portion 70, that is, on the end side whose thickness further decreases when the inflation portion 40 is inflated. Accordingly, it is possible to prevent the inflation and deformation of the inflation portion 40 from being hindered by the projection portion 70.

As illustrated in the enlarged view in FIG. 2, the projection portion 70 is disposed in the second region A2. The projection portion 70 is joined at a position where the rigid portion 50 configuring the second region A2 and the band 20 (belt 21) overlap each other. As a method of joining the projection portion 70 and the rigid portion 50, and the projection portion 70 and the band 20, in view of a material of each member as the joining target it is possible to employ a method such as adhesion using an adhesive, welding, and fusion bonding, for example.

Note that, the projection portion 70 may be disposed in the first region A1, or may be disposed across the first region A1 and the second region A2.

For example, the projection portion 70 can be formed of an elastic material. For example, the elastic material includes various rubber materials such as natural rubber, butyl rubber, isoprene rubber butadiene rubber, and styrene-butadiene rubber. Note that, it is preferable that the projection portion 70 is formed of a relatively flexible elastic material so as not to hinder the dilating deformation and the deflating deformation of the inflation portion 40.

A position of disposing the second region A2 and the projection portion 70 in the first sheet 41 is not particularly limited as long as the gas can be discharged from the second region A2. However, when hemostasis is performed using the hemostatic device 10 if the second region A2 or the projection portion 70 is disposed at a position overlapping the puncture site P, there is a possibility that a position of the marker 40c may be less likely to be visually recognized or that a compressing force may be unexpectedly applied to the puncture site P from the projection portion 70. Therefore, it is preferable that the second region A2 and the projection portion 70 are disposed at a position shifted to the end portion side (lateral direction in FIG. 5) of the inflation portion 40 from the central portion of the inflation portion 40. Furthermore in order to prevent the gas discharged from the inflation portion 40 from staying between the inflation portion 40 and the band 20 (belt 21), it is preferable that the second region A2 and the projection portion 70 are disposed at a position closer to the end portion side (leftward direction in FIG. 5) opposite to the interlock region 21b side where the inflation portion 40 and the band 2 interlock with each other, as illustrated in FIG. 5.

As illustrated in FIG. 5, the inflation portion 40 is disposed on the inner surface side of the band 20. Therefore, if the inflation portion 40 is inflated, the band 20 restrains the inflation portion 40 from being inflated in a direction separated from the body surface of the wrist W. In this manner, the compressing force of the inflation portion 40 is concentrated on the wrist W side. Accordingly, it is possible to suitably apply the compressing force to the puncture site P. In addition, the inflation portion 40 is wrapped around the wrist W by the band 20, and the internal pressure increases. Accordingly the gas contained inside the inflation portion 40 can be suitably discharged outward. Furthermore, it is possible to suitably prevent the discharge of the gas contained inside the inflation portion 40 from being hindered in such a way that a wearer wearing the hemostatic device 10 inadvertently touches the micropore 51 of the second region A2.

In addition, as illustrated in FIG. 5, the inflation portion 40 is disposed at a position overlapping the first curved portion 22b of the support plate 22. Therefore, when the inflation portion 40 is inflated, the support plate 22 restrains the inflation portion 40 from being inflated in a direction separated from the body surface of the wrist W. Accordingly, the compressing force of the inflation portion 40 is concentrated on the wrist W side. As described above, in the hemostatic device 10, the projection portion 70 adjusts the compressing direction of the inflation portion 40 so as to face the puncture site P, and the support plate 22 concentrates the compressing force on the puncture site P. Accordingly, the hemostatic device 10 can suitably perform hemostasis on the puncture site P. Note that, for the convenience of illustrating a configuration of the projection portion 70, FIG. 5 illustrate a state where the inflated and deformed inflation portion 40 is not in contact with the band 20. However, the inflation portion 40 can be configured to be inflated and deformed to such an extent that the inflation portion 40 receives a support force from at least the support plate 22.

It is preferable that the inflation portion 40 is substantially transparent. However, without being limited to transparency, the inflation portion 40 may be translucent or colored transparent. In this manner, the puncture site P is visible from the outer surface side, thereby enabling the marker 40c (to be described later) to easily align with the puncture site P.

As illustrated in FIG. 2, on the inner surface of the inflation portion 40, the marker 40c is disposed at substantially center (substantially the center of the second sheet 42) on the outer surface side disposed on the wrist W side. Since this marker 40c is dis posed in the inflation portion 40, the inflation portion 40 can easily, align with the puncture site P. Accordingly, it is possible to restrain misalignment of the inflation portion 40. In addition, since the marker 40c is disposed on the inner surface side of the inflation portion 40, the marker 40c does not directly come into contact with the puncture site P. Note that, a position for disposing the marker 40c is not particularly limited as long as the inflation portion 40 can align with the puncture site P For example, in the inflation portion 40, the marker 40c may be disposed at substantially the center (substantially the center of the first sheet 41) on the outer surface side disposed on the band 20 side.

Without being particularly limited, a shape of the marker 40c includes circular, triangular, and square shapes, for example. In the exemplary embodiment, the marker 40c has the square shape.

A size of the marker 40c is not particularly limited. However, for example, in a case where the shape of the marker 40c is the square shape, itis preferable that one side length thereof is in a range of 1 to 4 mm. If one side length is 5 mm or longer the size of the marker 40c is larger than the size of the puncture site P. Consequently, the central portion of the inflation portion 40 is less likely to align with the puncture site P.

Without being particularly limited, a material of the marker 40c includes oily colorants such as ink and resins kneaded with pigments.

A color of the marker 40c is not particularly limited as long as the color enables the inflation portion 40 to align with the puncture site P. However, it is preferable that the color is a green color system. If the green color system is used, the marker 40c is easily visible on the blood or the skin. Accordingly, the inflation portion 40 is much likely to align with the puncture site P.

In addition, it is preferable that the marker 40c is translucent or colored transparent. In this manner, the puncture site P is visible from the outer surface side of the marker 40c.

A method of disposing the marker 40c in the inflation portion 40 is not particularly limited. However, for example, the method includes a method of printing the marker 40c on the inflation portion 40, and a method of attaching the marker 40c to the inflation portion 40 by applying an adhesive to one side surface of the marker 40c.

The injection portion 60 is used for injecting the gas into the inflation portion 40. As illustrated in FIG. 1, the injection portion 60 is connected to the inflation portion 40.

The proximal portion of the injection portion 60 is connected to the inflation portion 40. The injection portion 60 includes a flexible tube 61 whose lumen communicates with the inside of the inflation portion 40, a bag 62 which is disposed in the distal portion of the tube 61 so as to communicate with the lumen of the tube 61 and which has a check valve (not illustrated) incorporated therein, and a tubular connector 63 connected to the bag 62.

As illustrated in FIG. 3(C), the tube 61 is connected to the inflation portion 40 so as to be interposed between the protruding portion 41c of the first sheet 41 and the protruding portion 42c of the second sheet 42. However, a position connected to the tube 61 in the inflation portion 40 is not particularly limited as long as the lumen of the tube 61 communicates with the internal space of the inflation portion 40.

When the inflation portion 40 is inflated (inflated), a distal tubular portion of a syringe (not illustrated) is inserted into the connector 63 so as to open the check valve. A plunger of the syringe is pressed, and the gas contained in the syringe is injected into the inflation portion 40 via the injection portion 60. If the inflation portion 40 is inflated, the bag 62 communicating with the inflation portion 40 via the tube 61 is inflated. It is possible to visually confirm that the inflation portion 40 can be pressurized without leakage of the gas. If the distal tubular portion of the syringe is removed from the connector 63 after the gas is, injected into the inflation portion 40, the check valve incorporated n the connector 63 is closed, thereby preventing the leakage of the gas.

Next, a method of using the hemostatic device 10 according to the exemplary embodiment will be described.

Before the hemostatic device 10 is worn on the wrist W, the inflation portion 40 is in a non-inflated state as illustrated in FIG. 2. As illustrated in FIGS. 4 and 5, in a case where the radial artery R of the wrist W of the right hand is punctured, the puncture site P is located at a position close to the thumb side. Normally, the introducer sheath is caused to indwell the puncture site P. The band 20 is wrapped around the wrist W left in a state where this introducer sheath indwells the puncture site P. The inflation portion 40 and the band 20 are aligned with each other so that the marker 40c disposed in the inflation portion 40 overlaps the puncture site P from above. The male side 31 and the female side 32 of the surface fastener 30 are brought into contact pith and joined to each other. In this manner, the band 20 is worn on the wrist W.

In this case, the hemostatic device 10 is worn on the wrist W so that the injection portion 60 faces the downstream side (palm side) of the blood flow in the radial artery R. In this manner, the injection portion 60 can be operated without interfering with a manual skill on the upstream side from the wrist or an instrument (for example, a blood pressure monitor) located on the upstream side. In addition, the hemostatic device 10 is worn on the wrist W of the right hand so that the injection portion 60 faces downstream side. In this manner, the inflation portion 40 is located in the radial artery R located close to the thumb side of the wrist W. Note that, in a case of the artery, the upstream side of the blood vessel indicates a direction closer to the heart of the blood vessel. In addition, the downstream side of the blood vessel indicates a direction farther away from the heart of the blood vessel.

Note that, the hemostatic device 10 may be used in a case where the radial artery of the wrist of the left hand is punctured. In this case, the injection portion 60 is worn on the wrist W of the left hand so as to face the upstream side of the blood flow in the radial artery.

After hemostatic device 10 is worn on the wrist W, the syringe (not illustrated) is connected to the connector 63 of the injection portion 60. As described above, the gas is injected into the inflation portion 40, and the inflation portion 40 is inflated.

In this case, an injection amount of the as is adjusted in accordance with a clinical case. In this manner, an inflated degree of the inflation portion 40, that is, the compressing force acting on the puncture site P can be easily adjusted. For example, in a case where the inflation portion 40 is excessively inflated since the gas injected too much into the inflation portion 40, the extra gas may be discharged from the inside of the inflation portion 40 by using the syringe.

After the inflation portion 40 is inflated, the syringe is detached from the connector 63. Then, the introducer sheath is removed from the puncture site P.

After the inflation portion 40 is inflated, the compressing force is applied to the puncture site P via the micropore 51 of the second region A2 as illustrated by a broken line arrow in FIG. 5. The gas contained inside the inflation portion 40 is discharged outward from the inflation portion 40 with the lapse of time to such an extent that the vascular occlusion can be prevented. The air discharged from the inflation portion 40 is sent to the gap g1 via the space S1 and the gas discharge path 71 of the projection portion 70.

Note that, in a case where the hemostasis is not sufficiently performed after the inflation portion 40 is inflated, the internal pressure of the inflation portion 40 may be increased by injecting additional gas into the inflation portion 40. For example, in a case here the internal pressure of the inflation portion 40 needs to restore the internal pressure to when the gas is injected into the inflation portion 40, additional gas may be injected to correspond to the amount of gas discharged from the inflation portion 40.

If the hemostasis completely performed on the puncture site P after a predetermined time elapses, the hemostatic device 10 is detached from the wrist W. The hemostatic device 10 is detached from the wrist W by separating the male side 31 and the female side 32 of the surface fastener 30 from each other.

As described above, the hemostatic device 10 according to the exemplary embodiment has the band 20 for being wrapped around the puncture site P of the wrist W, the securing means 30 for securing the band 20 in a state where the band 20 is wrapped around the wrist W, and the inflation portion 40 that interlocks with the band 20, and that is inflated by injecting the gas. In addition, the inflation portion 40 includes the first region A1 which stretches when the gas is injected into the inflation portion 40 and the second region A2 which is much less likely to stretch than the first region A1 and which is formed of the rigid material. The second region A2 has the micropore 51 which discharges the gas contained inside the inflation portion 40 with the lapse of time, in a state where the inflation portion 40 is inflated.

As described above, the micropore 51 of the inflation portion 40 is disposed in the second region A2 which is more rigid than the first region A1. In this manner, before and after the inflation portion 40 is inflated, in the micropore 51, the inner diameter of the micropore 51 and the channel length (length in the thickness direction of the inflation portion) are less likely to be changed. Therefore, in view of the viscosity of the gas used for dilating the inflation portion 40, the inner diameter of the micropore 51 is formed to have a predetermined size. In this manner, it is possible to easily adjust a gas discharge rate of the inflation portion 40. Furthermore, the gas is discharged from the second region A2 via the micropore 51. Accordingly, it is not necessary to manufacture the inflation portion so that the thickness of the inflation portion becomes thinner with the lapse of time. Therefore, the hemostatic device 10 according to the exemplary embodiment of the disclosure can satisfactorily maintain strength of the inflation portion 40, and easily perform decompressing adjustment for reducing the compressing force with the lapse of time in accordance with the progress of the hemostasis while preventing the vascular occlusion.

In addition, in the hemostatic device 10, the first region A1 is formed of the resin material, and the second region A2 is formed of the metal material. In the inflation portion 40, the first region A1 is formed of the resin material. Accordingly, the inflation portion 40 is inflated and deformed by injecting the gas into the inflation portion 40, thereby enabling the compressing force to be applied to the puncture site P. The inflation portion 40 is deflated and deformed by discharging the gas from the inflation portion 40, thereby enabling the compressing force applied to the puncture site P to be reduced. Furthermore in the inflation portion 40, the second region A2 is formed of the metal material. Accordingly, it is possible to prevent the second region A2 from being deformed during the hemostasis. The micropore 51 having a desired inner diameter can be easily formed in the second region A2 by using a method such as laser irradiation. Moreover, it is possible to, prevent the gas permeation from occurring based on the gas dissolution and diffusion phenomenon in the second region A2. Accordingly, decompressing adjustment is more easily performed using the micropore 51.

In addition, the inflation portion 40 has the projection portion 70 disposed so as to surround the micropore 51. The projection portion 70 has the gas discharge path 71 which can discharge the gas discharged from the inflation portion 40 through the micropore 51, in a state where the inflation portion 40 is inflated. The projection portion 70 forms the space S1 around the micropore 51. The space S1 prevents fine foreign substances such as dust and dirt from adhering to the vicinity of the micropore 51, and prevents the gas discharge through the micropore 51 from being hindered by the foreign substances clogging the micropore 51. Furthermore, the gas discharged from the inflation portion 40 can be discharged outward from the space S1 via the gas discharge path 71 of the projection portion 70. In this way, the projection portion 70 can perform decompressing adjustment on the inflation portion 40 while preventing the micropore 51 from being clogged by the foreign substances.

In addition, the projection portion 70 is disposed in the second region A2. Therefore, the projection portion 70 is stably supported in the relatively rigid second region A2. Accordingly, misalignment of the inflation portion 40 is less likely to occur before and after the inflation portion 40 is inflated and deformed.

In addition, the second region A2 has the plurality of micropores 51a. Therefore, the gas discharge rate of the second region A2 can be accurately adjusted by adjusting the inner diameter of each micropore 51 included in the plurality of micropores 51a and the number of micropores 51.

Next, modified examples of the above-described exemplary embodiment will be described. Note that, in describing each modified example, the same reference numerals will be given to configurations which are the same as those according to the above-described exemplary embodiment, and description thereof will be omitted.

Figure 6:
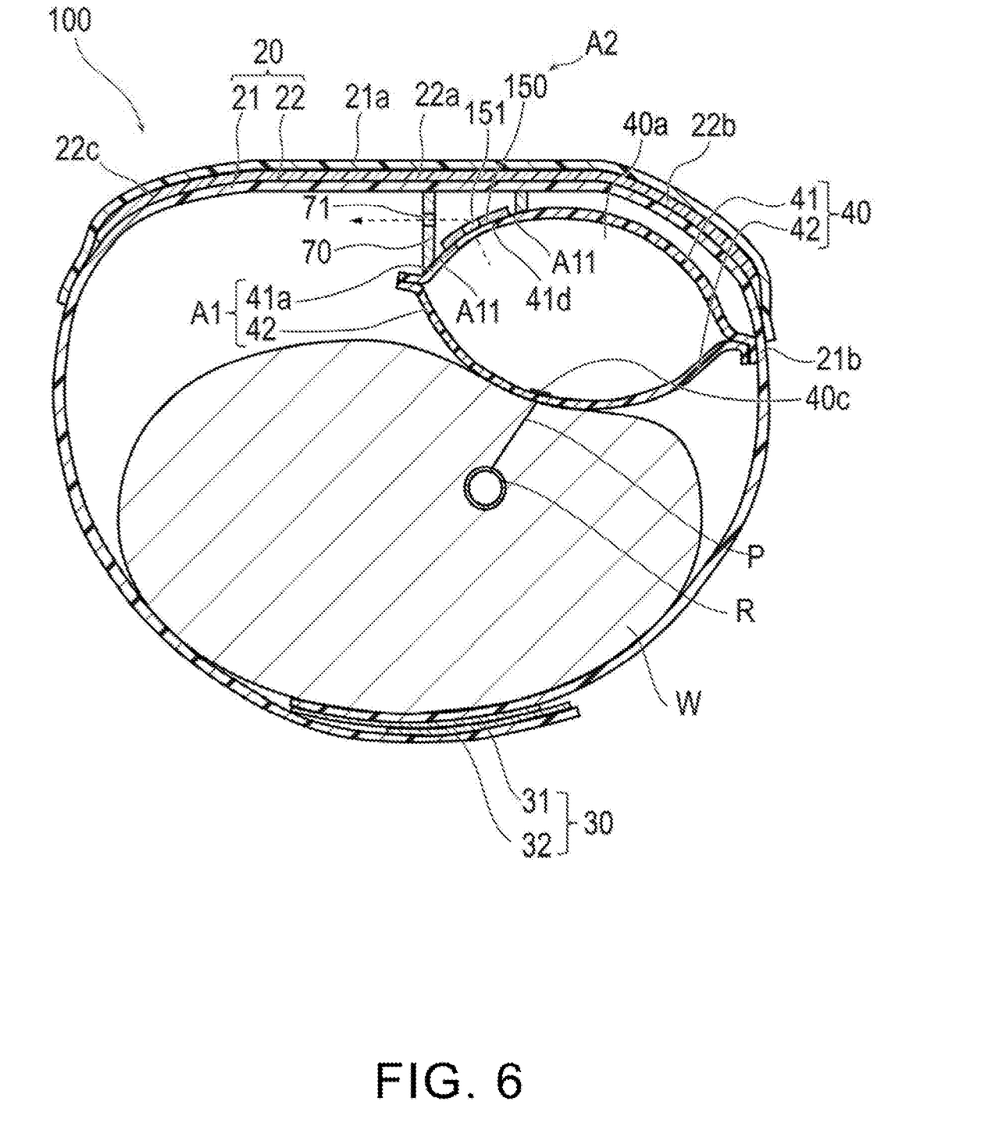
FIG. 6 is a sectional view illustrating a hemostatic device according to a first modified exemplary embodiment.

FIG. 6 is a view for describing a hemostatic device 100 according to a first modified exemplary embodiment according to the disclosure.

The hemostatic device 100 according to the first modified exemplary embodiment has a configuration of the second region A2 of the inflation portion 40 which is different from that according to the above-described exemplary embodiment. Specifically, as illustrated in FIG. 6, in the cross section (cross section illustrated in FIG. 6 taken along the dilating direction of the inflation portion 40, the second region A2 is disposed closer to an inner surface side of the band 20 than a portion A11 (partial range of the first region A1) of the first region which is disposed around the second region A2.

The second region A2 is configured to include a rigid portion 150 of the first sheet 41. The rigid portion 150 has a micropore 151 which discharges the gas from the inflation portion 40. Note that, although not illustrated, according to the first modified exemplary embodiment, the second region A2 also has, the plurality of micropores.

According to the above-described exemplary embodiment the projection portion 70 is joined to the second region A2 (rigid portion 150). However, according to the first modified exemplary embodiment, the projection portion 70 is disposed in (joined to) the first region A1. However, according to the hemostatic device 100 in the present modification example, the projection portion 70 can also be disposed in the second region A2.

A material of the rigid portion 150 configuring the second region A2 and a method of forming (method of joining) the rigid portion 150 in the first sheet 41 are the same as those according to the above-described exemplary embodiment. As a method of joining the first region A1 and the projection portion 70 to each other, in view of a material of each member, it is possible to employ a method such as adhesion using an adhesive and fusion bonding, for example.

In a sectional view illustrated in FIG. 6, a portion having the micropore 151 of the second region A2 is disposed closer to an inner surface side of the band 20 than the portion A11 disposed around the second region A2 of the first region A1. Therefore, a step is formed along the dilating direction of the inflation portion 40 between the portion having the micropore 151 of the second region A2 and the portion A11 of the first region A1, which is disposed around the second region A1 Even if a water droplet or dirt adheres to the vicinity of the portion having the micropore 151 of the second region A2, the water droplet or the dust is guided to the above-described step side. Accordingly, the water droplet or the dust is less likely to stay around the micropore 151. In this manner, it is possible to more reliably prevent the micropore 151 from being clogged by the water droplet or the dust.

Note that, a sectional shape and thickness of the rigid portion 150 configuring the second region A2, and a distance in which the second region A2 is separated from the first region A1 around the second region A2 are not particularly limited as long as the water droplet or the dirt can be restrained from entering the inflation portion 40.

Figure 7:
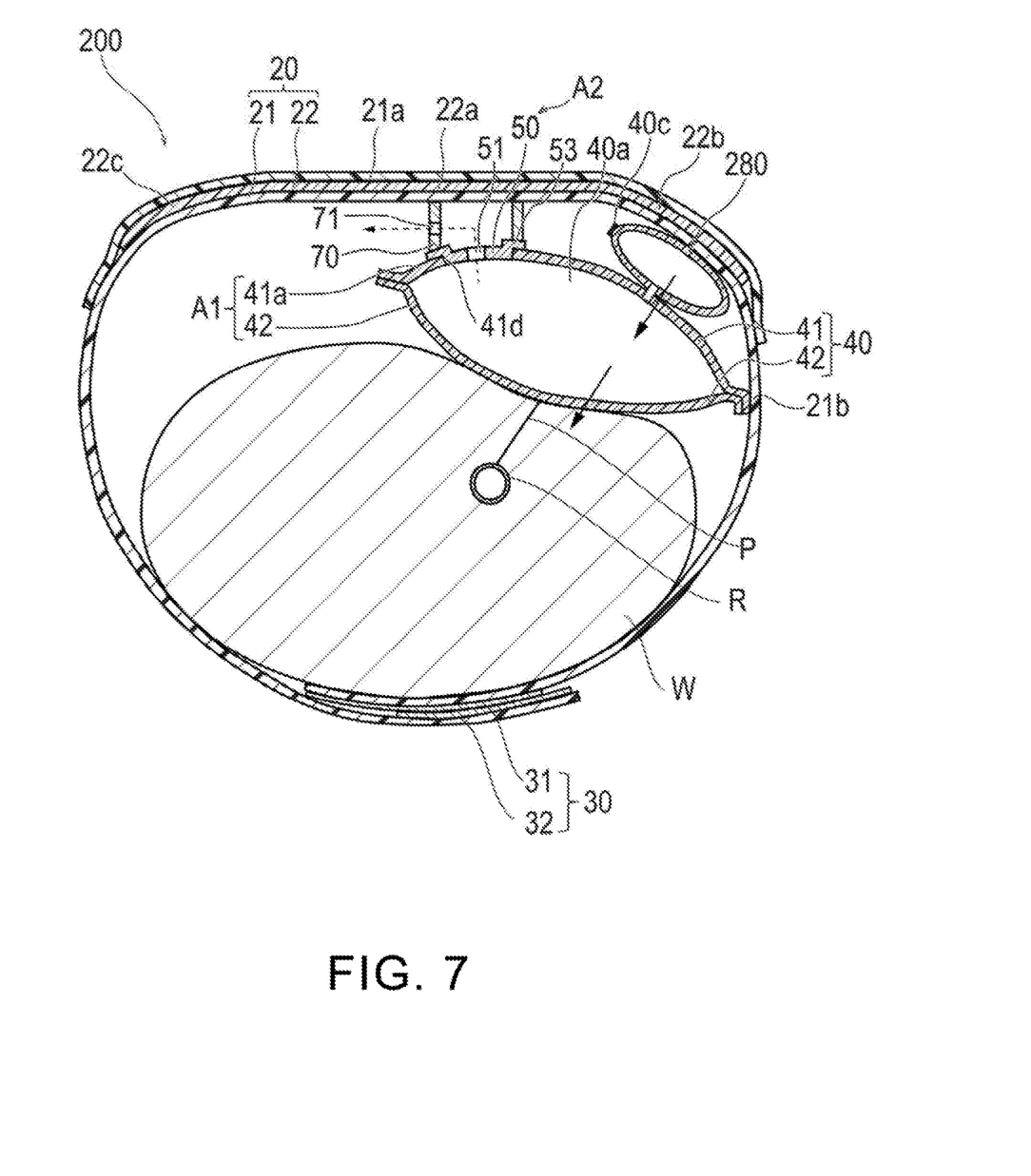
FIG. 7 is a sectional view illustrating a hemostatic device according to a second modified exemplary embodiment.

FIG. 7 is a view for describing a hemostatic device 200 according to a second modified exemplary embodiment according to the disclosure.

The hemostatic device 200 according to the second modified exemplary embodiment is different from that according to the above-described exemplary embodiment in that an auxiliary compression portion 280 is provided between the inflation portion 40 and the band 20 and in that the marker 40c is disposed in the auxiliary compression portion 280.

The auxiliary compression portion 280 is formed in a bag shape, similar to the inflation portion 40. The auxiliary compression portion 280 is attached to the inflation portion 40 so that the internal space communicates with the inflation space 40a of the inflation portion 40. Therefore if the gas is injected into the inflation portion 40, the auxiliary compression portion 280 is also inflated.

It is preferable that the auxiliary compression portion 280 is configured to include a resin material other than a thermosetting elastomer. As described above, in general, the thermosetting elastomer has more gas permeation amount based on the gas dissolution and diffusion phenomenon than the thermoplastic material. Accordingly, if the auxiliary compression portion 280 is configured to include the thermosetting elastomer a gas discharge amount discharged from the auxiliary compression portion 280 increases. For this reason, the micropore 51 is less likely to adjust the gas discharge amount. Therefore, it, is preferable that the auxiliary compression portion 280 is formed of the resin material other than the thermosetting elastomer.

Note that, the auxiliary compression portion 280 may be configured to include a sponge-like substance, an elastic material, an aggregate of fibers such as cotton, or a combination thereof.

The marker 40c is disposed in an end portion on a side close to the center of the inflation portion 40 on the outer surface of the auxiliary compression portion 280. Since this marker 40c is disposed in the auxiliary compression portion 280, the inflation portion 40 can easily align with the puncture site P. Accordingly, misalignment of the inflation portion 40 is restrained. In addition, since the marker 40c is disposed in the auxiliary compression portion 280 the gas permeation in the second region A2 of the inflation portion 40 is not hindered. Note that, a position for disposing the marker 40c is not particularly limited as long as the inflation portion 40 can align with the puncture site P. For example, the marker 40c may be disposed in the inflation portion 40.

According to the hemostatic device 200 in the second modified exemplary embodiment described above, as illustrated by a solid line arrow in FIG. 7, the auxiliary compression portion 280 can adjust a direction of the compressing force applied by the inflation portion 40 so as to be a direction oriented to the puncture site P.

Note that, the auxiliary compression portion 280 described in the second modified exemplary embodiment can also be disposed in the hemostatic device 100 described as the first modified exemplary embodiment.

Note that, for example, the projection portion 70 can be provided with a function of the auxiliary compression portion 280 by disposing the projection portion 70 at a position of the auxiliary compression portion 280 in FIG. 7. Since the projection portion 70 is disposed at this position, the projection portion 70 can adjust the direction of the compressing force so as to be the direction oriented to the puncture site P. Accordingly, it is possible to improve a hemostasis effect achieved by the inflation portion 40.

Hitherto, the hemostatic device according to the disclosure herein has been described with reference to the exemplary embodiment and the modified exemplary embodiments. However, without being limited to only the respectively described configurations, the disclosure can be appropriately modified based n the description in the appended claims.

For example, each portion configuring the hemostatic device can be substituted with any optional configuration which can fulfill the same function. In addition, any optional configuration element may be added thereto.

In addition, without being limited to the hemostatic device used by being worn on the wrist, the disclosure herein is also applicable to a hemostatic device used by being worn on a leg.

In addition, according to the above-described exemplary embodiment, the hemostatic device includes the projection portion. However, for example, the hemostatic device may not include the projection portion.

In addition, according to the above-described exemplary embodiment, the inflation portion is configured to include two sheets. However, the configuration is not particularly limited as long as the inflation portion includes the first region which is inflated by injecting the gas and the second region which is much less likely to stretch than the first region, and the inflation portion can be inflated by the gas. For example, the inflation portion may be configured to include a single sheet, and may be formed in a bag shape in such a way that the sheet is folded and edge portions thereof are bonded or fused to each other. In addition, the inflation portion may be configured to include a balloon-like member which does not include the edge portion.

In addition, the first region may be disposed in a portion interlocking with at least the band in the inflation portion. In addition a position for disposing the second region is not particularly limited as long as the gas can be discharged from the inflation portion via the micropore of the second region. For example, the second region may be disposed on both the inner surface disposed on the limb side and the outer surface disposed on the band side. Alternatively, the second region play be disposed on only the inner surface.

The detailed description above describes features and aspects of embodiments of a hemostatic device. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A hemostatic device comprising:
   a band adapted to be wrapped around a limb of a patient at a site on the limb where bleeding is to be stopped;
   securing means for securing the band in a wrapped state around the limb; and
   an inflation portion disposed on an inner peripheral surface of the band, and adapted to be inflated by injecting gas;
   wherein the inflation portion includes a first region adapted to stretch when the gas is injected into the inflation portion, and a second region formed of a rigid material and adapted to stretch less than the first region; and
   wherein the rigid material of the second region has at least one micropore adapted to discharge the gas contained in the inflation portion with the lapse of time, in a state where the inflation portion is inflated.

2. The hemostatic device according to claim 1,
   wherein the first region is formed of a resin material, and
   wherein the second region is formed of a metal material.

3. The hemostatic device according to claim 1,
   wherein the inflation portion has a projection portion disposed so as to surround the at least one micropore, and
   wherein the projection portion has a gas discharge path to discharge the gas discharged from the inflation portion through the at least one micropore, in a state where the inflation portion is inflated.

4. The hemostatic device according to claim 3,
   wherein the projection portion is disposed in the second region.

5. The hemostatic device according to claim 3, wherein the projection portion is joined to the first region.

6. The hemostatic device according to claim 1,
   wherein, in a cross section taken along a dilating direction of the inflation portion, the second region is disposed closer to an inner surface side of the band than a portion of the first region which is disposed around the second region.

7. The hemostatic device according to claim 1,
   wherein the at least one micropore includes a plurality of micropores.

8. The hemostatic device according to claim 1, wherein the inflation portion interlocks with the band.

9. The hemostatic device according to claim 1, wherein the second region has a Young's modulus smaller than a Young's modulus of the first region.

10. The hemostatic device according to claim 1, wherein the at least one micropore is configured such that, after one hour elapses, an internal pressure of the inflation portion reaches 70%-97% of the internal pressure of the inflation portion at an immediately preceding hour.

11. The hemostatic device according to claim 10, wherein, after four hours elapsed time, the internal pressure of the inflation portion is 30%-80% of an initial internal pressure of the inflation portion.

12. The hemostatic device according to claim 1, wherein the band includes a flexible belt member and a support member, the inflation portion being disposed to overlap a portion of the support member.

13. The hemostatic device according to claim 1, further comprising an auxiliary compression portion disposed between the inflation portion and the band.

14. A hemostatic device comprising:
    a band configured to be wrapped around a limb of a patient at a site on the limb where bleeding is to be stopped;
    means for securing the band in a wrapped state to the patient's limb; and
    an inflation portion disposed on an inner peripheral surface of the band and configured to be inflated by injecting gas;
    wherein the inflation portion includes a first region formed from a material having a first Young's modulus and a second region formed from a material having a second Young's modulus, the second Young's modulus being smaller than the first Young's modulus such that the first region is configured to stretch more than the second region when gas is injected into the inflation portion; and wherein the material having the second Young's modulus of the second region has at least one micropore configured to discharge gas contained in the inflation portion over a predetermined period of elapsed time.

15. The hemostatic device according to claim 14, further comprising a marker for positioning the inflation portion at the site where bleeding is to be stopped.

16. The hemostatic device according to claim 15, wherein the marker is disposed on the inflation portion.

17. The hemostatic device according to claim 14, wherein the inflation portion includes a projection portion disposed so as to surround the at least one micropore, and the projection portion includes a gas discharge path to discharge gas that has been discharged from the inflation portion through the at least one micropore.

* * * * *